United States Patent [19]
Schwartz et al.

[11] Patent Number: 5,573,520
[45] Date of Patent: Nov. 12, 1996

[54] FLEXIBLE TUBULAR DEVICE FOR USE IN MEDICAL APPLICATIONS

[75] Inventors: Robert S. Schwartz; David R. Holmes, both of Rochester; Frederick S. Halverson, North Oaks; James V. Donadio, III, Chaska, all of Minn.; David Berry, Longmont, Colo.

[73] Assignee: Mayo Foundation for Medical Education and Research, Rochester, Minn.

[21] Appl. No.: 329,691

[22] Filed: Oct. 26, 1994

Related U.S. Application Data

[63] Continuation of Ser. No. 940,657, Sep. 4, 1992, abandoned, which is a continuation-in-part of Ser. No. 755,614, Sep. 5, 1991, abandoned.

[51] Int. Cl.$^6$ .................................................. A61M 25/00
[52] U.S. Cl. ........................... 604/282; 604/264; 128/772
[58] Field of Search .................................. 604/264, 280, 604/282, 164, 167, 169, 170; 128/656–658, 772

[56] References Cited

U.S. PATENT DOCUMENTS

| | | |
|---|---|---|
| 3,071,942 | 1/1963 | Alcaro . |
| 3,390,546 | 7/1968 | Jewell . |
| 3,598,126 | 8/1971 | Hoeltzenbein . |
| 3,844,137 | 10/1974 | Zugel . |
| 4,020,829 | 5/1977 | Willson et al. . |
| 4,465,482 | 8/1984 | Tittel . |
| 4,547,193 | 10/1985 | Rydell . |
| 4,580,551 | 4/1986 | Siegmund et al. . |
| 4,634,432 | 1/1987 | Kocak ..................................... 604/167 |
| 4,639,252 | 1/1987 | Kelly et al. . |
| 4,676,229 | 6/1987 | Krasnicki et al. . |
| 4,733,665 | 3/1988 | Palmaz . |
| 4,739,762 | 4/1988 | Palmaz . |
| 4,764,324 | 8/1988 | Burnham . |

(List continued on next page.)

FOREIGN PATENT DOCUMENTS

| | | |
|---|---|---|
| 0262735 | 4/1988 | European Pat. Off. . |
| 0364787 | 4/1990 | European Pat. Off. . |
| 4104092 | 8/1991 | Germany . |

OTHER PUBLICATIONS

Cole–Parmer Instrument Company, 1991–1992 catalogs, p. 888 (Grooved PTFE tubing).

Morton J. Kern, M.D., *Small Diameter Guiding Catheters for Coronary Angioplasty*, Cardio Intervention, Miller Freeman Pub., Apr. 1992, pp. 20–24.

J. David Talley, et al., *A Prospective Randomized Study of 4.1 French Catheters Utilizing the Percutaneous Right Brachial Approach for the Diagnosis of Coronary Artery Disease*, Catheterization and Cardiovascular Diagnosis, Wiley–Liss, Inc., vol. 26, pp. 55–60, 1992.

Katsumi Uneno, et al., *Coronary Angioplasty Using an Over–the–Wire Ballon Catheter Through a New 6 French Guiding Catheter*, Catheterization and Cardiovascular Diagnosis, Wiley–Liss, Inc. vol. 26, pp. 61–68, 1992.

Jan Voda, *Long–Tip Guiding Catheter: Successful and Safe for Left Coronary Artery Angioplasty*, Catheterization and Cardiovascular Diagnosis, Wiley–Liss, Inc., vol. 27, pp. 234–242, 1992.

Heather E. O'Connor et al., *Sitting Up Post Angioplasty: A New Sheath Technology*, Catheterization and Cardiovascular Diagnosis, Wiley–Liss, Inc., vol. 25, pp. 76–78, 1992.

*Primary Examiner*—John D. Yasko
*Attorney, Agent, or Firm*—Merchant, Gould, Smith, Edell, Welter & Schmidt Professional Association

[57] ABSTRACT

An apparatus for use as a catheter, a guidewire, a catheter sheath for use with catheter introducers or a drug infusion catheter/guidewire. The apparatus includes a flexible tubular member with an encasing covering the tubular member that creates a fluid-tight seal around the periphery of the tubular member. The tubular member is self-supporting and includes a plurality of apertures therein in a predetermined configuration to increase the flexibility of the tubular member.

18 Claims, 9 Drawing Sheets

U.S. PATENT DOCUMENTS

| | | |
|---|---|---|
| 4,776,337 | 10/1988 | Palmaz . |
| 4,842,590 | 6/1989 | Tanabe et al. . |
| 4,863,442 | 9/1989 | DeMello et al. ............... 604/282 |
| 4,893,623 | 1/1990 | Rosenbluth . |
| 4,898,591 | 2/1990 | Jang et al. ................. 604/282 |
| 4,911,148 | 3/1990 | Sosnowski et al. . |
| 4,921,482 | 5/1990 | Hammerslag et al. . |
| 4,932,419 | 6/1990 | de Toledo . |
| 4,998,923 | 3/1991 | Samson et al. . |
| 5,019,057 | 5/1991 | Truckai . |
| 5,052,404 | 10/1991 | Hodgson . |
| 5,065,769 | 11/1991 | de Toledo . |
| 5,069,674 | 12/1991 | Fearnot et al. . |
| 5,073,694 | 12/1991 | Tessier et al. . |
| 5,095,915 | 3/1992 | Engelson ....................... 128/772 |
| 5,102,417 | 4/1992 | Palmaz . |
| 5,107,852 | 4/1992 | Davidson et al. . |
| 5,131,406 | 7/1992 | Kaltenbach . |
| 5,178,158 | 1/1993 | de Toledo ....................... 128/772 |
| 5,180,376 | 1/1993 | Fischell . |
| 5,195,984 | 3/1993 | Schatz . |
| 5,209,741 | 5/1993 | Spaeth ........................ 604/264 |
| 5,221,270 | 6/1993 | Parker ........................ 604/282 |
| 5,228,441 | 6/1993 | Lundquist . |
| 5,234,416 | 8/1993 | Macaulay et al. ............. 604/282 |
| 5,275,152 | 1/1994 | Krauter et al. ............... 128/4 |
| 5,315,996 | 5/1994 | Lundquist . |
| 5,322,064 | 6/1994 | Lundquist . |
| 5,421,955 | 6/1995 | Lau et al. . |

FLEXIBLE TUBULAR DEVICE FOR USE IN MEDICAL APPLICATIONS

This is a continuation of application Ser. No. 07/940,657, filed Sep. 4, 1992, now abandoned, which was a continuation-in-part of application Ser. No. 07/755,614, filed Sep. 5, 1991, now abandoned.

BACKGROUND OF THE INVENTION

The present invention relates to a biscompatible flexible tubular device for insertion into the body during medical procedures. More particularly, the invention relates to flexible tubular devices for use as catheters, including guide catheters and balloon catheters, guidewires, catheter sheaths, catheter introducers, drug infusion catheters/guidewires, and methods for making the same.

Catheters and Guidewires

Catheters are relatively thin and flexible tubes used in the medical field for numerous applications. Catheters are made by any number of different methods and designs. However, in most catheter designs it is desirable to obtain a maximum torsional rigidity while retaining a satisfactory longitudinal flexibility and stiffness without kinking. These features will allow the orientation of the catheter to be manipulated so that the catheter can be guided through small body vessels and cavities. These features will also prevent any kinking from occurring, and provide the catheter with enough "push" or stiffness so as to prevent the catheter from wrinkling or folding back on itself during this process. The specific nature of these characteristics will of course vary depending on the specific application for which the catheter is being used. Yet another consideration is that a relatively small outside diameter must be maintained while providing a lumen or an inside diameter as large as possible.

Guide wires require the same general type of characteristics. However, with guide wires it is important to minimize the outside diameter of the guide wire so that they will readily fit inside of the lumen of the catheter.

Catheters and guide wires are used both as diagnostic tools and in the treatment of diseases. One such diagnostic procedure is cardiac catheterization which is a widely performed procedure, being used for assessment of coronary artery disease. Other uses are neurologic uses, radiologic uses, electrophysiologic uses, peripheral vascular uses, etc. One example of a treatment use is the use of balloon catheters in dilation procedures to treat coronary disease. Dilation procedures rely upon the use of a catheter for injection of contrast and delivery of guidewires and dilation catheters to the coronary artery or other arteries. An example of the use of guide wires is for Percutaneous Transluminal Coronary Angioplasty (PTCA) balloons and for guiding diagnostic catheters through the arteries and to body organs.

The catheters and guide wires used in these and other procedures must have excellent torque characteristics, and must have the requisite flexibility. In addition, it is important that catheters and guidewires provide sufficient longitudinal support for "pushing" of items through the arteries and other vessels such as when feeding the balloon portion of an angioplasty catheter through the arteries. Unless there is sufficient stiffness, the catheter or guidewire will wrinkle or fold back on itself.

Typically, in the case of a catheter, the larger the ratio of inside to outside diameter, the better. For guide wires it is important to maintain a small outside diameter. Smaller catheter and guidewire outside diameter sizes result in less chance of arterial damage.

Catheters and guide wires must have sufficient torque such that they do not buckle when being manipulated. Finally, flexibility is important so that the catheter or guide wire can be manipulated into the varying arterial branches encountered by the catheter. The guide wire must resist being inadvertently kinked as this results in loss of torque control.

Prior art catheters are typically made of flexible materials which are reinforced such that the resulting composite catheter approximates the desired characteristics. In alternative approaches, guide wires are used in conjunction with catheters to assist in manipulating and moving the catheters through the arterial system in the body.

U.S. Pat. No. 4,020,829 to Willson et al. discloses a spring guide wire for use in catheterization of blood vessels. The guide wire is axially slidable within a thin walled, flexible plastic catheter. The distal portion of the guide wire is of a relatively short length and is connected to a relatively long, manipulative section capable of transmitting rotational torque along its length. In this invention the catheter tube might be advanced over the guide wire after the guide wire has been properly positioned or the catheter might be advanced together with the guide wire, the guide wire providing a reinforcement for the thin wall of the catheter.

U.S. Pat. No. 4,764,324 to Burnham discloses a method for making a catheter. In Burnham, a reinforcing member is heated and applied to a thermoplastic catheter body so as to become embedded in the wall of the catheter. The wall of the catheter is then smoothed and sized so as to produce a composite, reinforced catheter.

The art of applying braiding or multi-pass wire reinforcement to a catheter inner core is also well developed and machinery for performing such a step is well known. Typically, such reinforcement material is applied to the inner core tube of the catheter in a pattern of overlapping right and left hand helices. The braiding process usually requires that the machinery performing the braiding process to move the reinforcement material alternately radially inwardly and outwardly, as well as circularly, whereby the tension of the reinforcement material continuously varies. This varying tension can result in the reinforcement material breaking particularly as the speed of braiding increases. Yet another problem with braided catheters is that their inside diameter is relatively small compared to their outside diameter. The braids are quite loose also.

Current catheters often suffer from either problems of torque, size, flexibility, kinking, and poor support during PTCA in the case of guide catheters. Moreover, catheters cannot be readily made with variable stiffness along the length of the catheter.

Catheter Sheaths and Introducers

Catheter sheaths and introducers are used to provide a conduit for introducing catheters, fluids or other medical devices into blood vessels. A catheter introducer typically comprises a tubular catheter sheath, a hub attached to the proximal end of the sheath having hemostasis valve means to control bleeding and to prevent air embolisms, and a removable hollow dilator that is inserted through the hub, valve means and the lumen of the catheter sheath. Many catheter introducers also contain a feed tube that is connected to the hub to facilitate the introduction of fluids into the blood vessel.

The procedure for positioning the introducer into a blood vessel begins by inserting a hollow needle through the skin and into the lumen of the desired blood vessel. A guidewire is then passed through the needle and into the blood vessel. The needle is then removed leaving the guidewire in the vessel. Next, the sheath and dilator are advanced together over the guidewire until the distal ends of the dilator and sheath are positioned within the lumen of the vessel. The guidewire and dilator are then removed, leaving the distal end of the sheath within the vessel. Catheters or other medical devices can then be passed through the introducer and sheath into the desired vessel.

Figure 14:
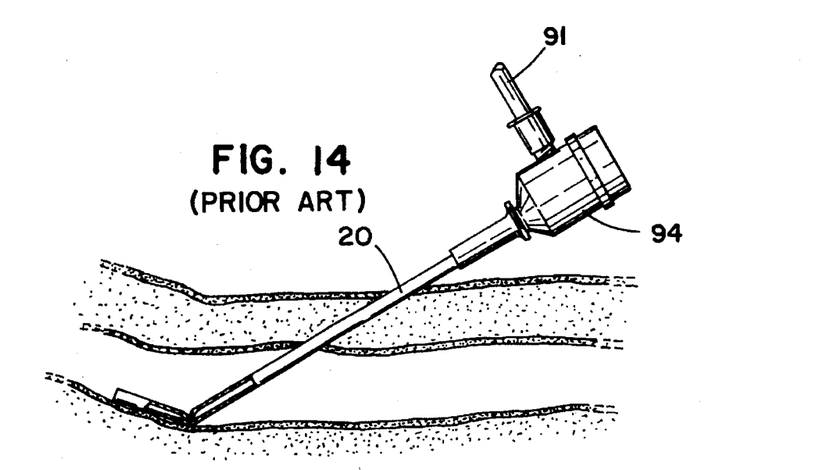
FIG. 14 is an elevational view of a prior art version of a catheter introducer with portions broken away after it has been advanced into a blood vessel of a patient and the dilator unit and guidewire have been withdrawn, showing a kinked catheter sheath.

Conventional sheaths are made of plastic and as shown in FIG. 14, are subject to kinking if bent without internal support. This kinking can occur during the insertion of the device or if the patient moves while the sheath is in the vessel. Unfortunately, this kinking can create sharp edges or irregularities in the sheath that can damage blood vessel linings. This kinking can also make the introduction of devices or fluids more difficult and can cause patient bleeding problems around the sheath tubing. Therefore, there arises a need for a catheter introducer with a catheter sheath that is flexible and resistant to kinking.

Conventional catheter sheaths also have a limited hoop strength making them susceptible to burring or notching. This burring and notching can occur during the insertion of the sheath and dilator into the blood vessel or if the forces exerted on the sheath cause it to become noncircular. These burrs and notches can also damage blood vessel linings. Therefore, there arises the need for a catheter sheath that has sufficient hoop strength to prevent deformation in the sheath to resist the formation of burrs or notches.

It is also important that the sheath have a minimum thickness to reduce the size of the puncture hole in the blood vessel. Larger puncture holes make hemostasis more difficult upon removal of the sheath. The sheath should also be lubricous to make the insertion and extraction of the sheath and other devices easy. Therefore, there arises the need for a catheter sheath for use with a catheter introducer that has a thin wall, that is flexible and resistant to kinking, that is lubricous, and that has sufficient hoop strength to prevent the catheter sheath from burring or notching.

One method for creating a sheath that may meet the above requirements would be to make the sheath from expanded polytetrafluoroethylene (PTFE) as disclosed in U.S. Pat. No. 5,066,285. While PTFE is more flexible and has a higher hoop strength than the plastics used in conventional sheaths, it is still a plastic-type material that may be subject to the same deformation problems.

Drug Infusion Catheters/Guidewires

Drug infusion catheters/guidewires are devices that act like both catheters and guidewires and are capable of delivering drugs or other fluids to a specific location within a patient's blood vessel such as an occluded blood vessel. The guidewire type devices are typically comprised of a coil spring with a heat shrunk TEFLON® coating and a core wire that can be inserted and removed from the lumen in the coil spring. The coated coil also contains either side holes or an end hole or a combination thereof in its distal end to enable the drugs or other fluids to be sprayed into the blood vessel.

During use, the coated coil spring and its core wire are advanced together through the patient's circulatory system much like conventional guidewires. Upon reaching the desired location, the core wire is removed creating a small catheter like device. Drugs or other fluids are pumped through the lumen in the coated coiled spring, out of the holes and into the blood vessel at the desired location.

Because these devices act like guidewires, the outside diameter of the devices, and therefore the lumen, are limited in size. Therefore, a second type of drug infusion catheter/ guidewire device utilizes a catheter like member with side holes and a tapered distal end having an end hole generally equal to the outside diameter of a guidewire. These catheter type drug infusion catheter/guidewire devices are advanced over a guidewire to the desired location and then drugs are then pumped through and out of the holes in the catheter like member. These devices can also be used in combination with the guidewire type drug infusion devices.

As described above, drug infusion catheter/guidewire devices act like both catheters and guidewires. Therefore, these devices must have the same characteristics as catheters and guidewires. These devices must obtain a maximum torsional rigidity while retaining a satisfactory longitudinal flexibility and stiffness without kinking. They must also maintain a small outside diameter while providing a lumen as large as possible.

SUMMARY OF INVENTION

The present invention relates to a novel apertured flexible tubular member with an encasing for insertion into vessels of the body as part of a medical device. For example, the invention can be used as catheters, including guide catheters and balloon catheters, guidewires, catheter sheaths for use with catheter introducers, or drug infusion catheter/ guidewires.

The preferred embodiment of the present invention will be coated with a low friction material such as a low friction polymer so as to provide for lubricity. Samples of materials that might be used are polyurethane, hydrogels, polyethylene, polytetrafluoroethylene (PTFE) and, in particular, one such material which might be used is TEFLON®.

In some embodiments, such as catheters or sheaths, the inside of the flexible tubular member is also preferably coated with a low friction material such as hydrogel and/or with an anticoagulant such as heparin. The coating process might be accomplished by any number of well known processes.

In yet another embodiment of the invention, slots of a predetermined configuration are cut into a single, hollow, thin walled metal tube at predetermined spacings, depth and pattern so as to provide the tube with a desired flexibility. The tube is then encased in a suitable low friction material as noted above or some other suitable coating material.

The use of the flexible tubular member within a fluid-tight encasing provides flexibility to catheters, guidewires, catheter sheaths and drug infusion catheter/guidewires without subjecting them to the possibility of kinking. In addition, because metal tube is used, these devices also have high hoop strength, therefore, they are resistant to the forming of burrs or notches. Catheter sheaths made from the present invention can also be adapted for use with any conventional catheter introducer parts to create an improved catheter introducer device.

The present invention is further explained hereafter with more particularity and reference to the preferred embodiment shown in the following drawings.

DETAILED DESCRIPTION OF THE DRAWINGS

In the drawings wherein like reference numerals indicate corresponding parts throughout the several views.

DETAILED DESCRIPTION OF THE PREFERRED EMBODIMENT

Figure 1:
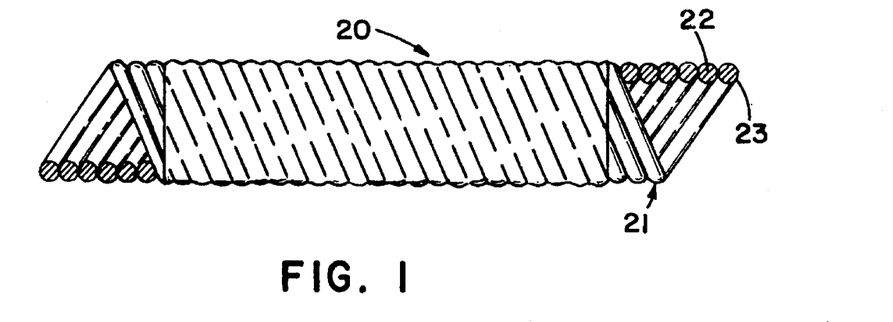
FIG. 1 is a partial view of an embodiment of a catheter, guidewire, catheter sheath or drug infusion catheter/guidewire in accordance with the principles of the invention wherein individual wound filaments comprise substantially round wire.
Figure 2:
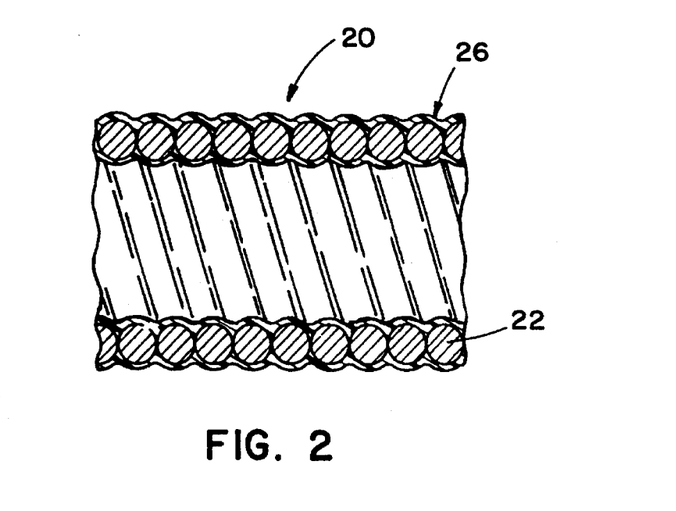
FIG. 2 is a sectional view of the embodiment shown in FIG. 1.
Figure 3:
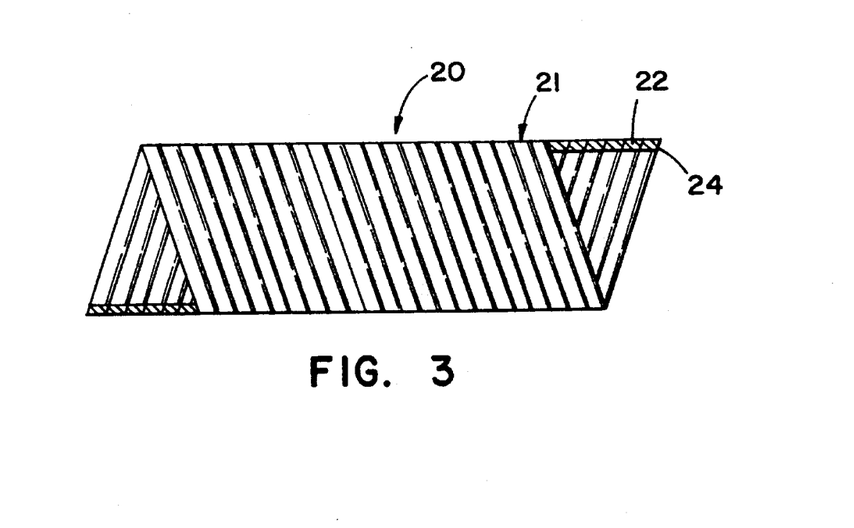
FIG. 3 is a partial view of an alternative embodiment of the present invention wherein the filaments comprise substantially flat ribbon.

Referring now to the drawings, FIGS. 1–3 illustrate two embodiments of a coated flexible tubular member in accordance with the principles of the present invention, generally referred to by the reference numeral 20, for use as a catheter, guidewire, catheter sheath or drug infusion catheter/guidewire. As illustrated in FIGS. 1 and 2, the flexible tubular member 20 has a single layer multiwire coil 21 including six wire filaments 22 which in this case comprise substantially round wire. It will be appreciated that differing numbers of filaments might be used; e.g. two to sixteen or more. In one embodiment, the filaments 22 are made of spring tempered, stainless steel. In another embodiment, the filaments are made of nitinol or ELGILOY®, which is a cobalt-nickel-chromium alloy. The diameter of the wire, in the embodiment shown, is preferably 0.002 inches to 0.010 inches. It will also be appreciated that a single filament coil or multi-layer coil could be used with the invention.

As illustrated, both of the embodiments shown in FIGS. 1–3 are preferably encased in a low friction material such as a low friction polymer or hydrogel for lubricity and to decrease thrombogenicity. Examples of materials which might be used are polyurethane, polyethylene, PTFE or TEFLON®. The thickness of this coating is typically 0.010 inches or less. Preferably the thickness of the coating will be less than the thickness of the filaments. The coating could be applied in one of any well-known methods, such as dip coating, heat shrinking, spray depositing or vapor depositing the material to the coil 21.

Illustrated in FIG. 3, is a helically wound, single layer multiwire coil 21 wherein the filaments 22 are made of flat ribbon 24. It will be appreciated that by varying the configuration of the multi-wire coil, a coated flexible tubular member 20 of varying characteristics can be formed. For example, making the individual coils more circular will result in a flexible tubular member 20 which has a greater hoop strength and stiffness, while making the individual coils more longitudinally extending will result in less hoop strength but more flexibility. Having fewer filaments, will result in increased flexibility but less hoop strength. Increasing the size of the filaments will result in increased hoop strength but less flexibility.

Moreover, varying the configuration of the multi-wire coil along the length of the flexible tubular member 20 can result in a flexible tubular member 20 with varying characteristics. For example, the middle section of the flexible tubular member 20 could be made more flexible by reducing the diameter, reducing the number of filaments, increasing the spacing between filament coils, etc., while the distal end of a flexible tubular member 20 could be arranged to have a higher hoop strength to prevent burring or notching. A flexible tubular member 20 could also be made where the distal end is very flexible and the proximal end is very stiff to improve the transmission of a torque at the proximal end to the distal end. Moreover, a flexible tubular member 20 can be made which varies in stiffness continuously throughout its length. A flexible tubular member 20 can also be made wherein the variation in flexibility or stiffness from one location to the next is very gradual and continuous.

In addition, the flexibility of the flexible tubular member 20 could also be reduced by selectively welding adjacent windings of the coil 21. By welding adjacent windings, the relative movement between the windings is eliminated and the flexibility of the coil in the area adjacent to the weld would be reduced. Therefore, a flexible tubular member 20 having variable flexibility along its length could be made from a coil 21 with a single winding configuration that had selective windings welded together.

Figure 4:
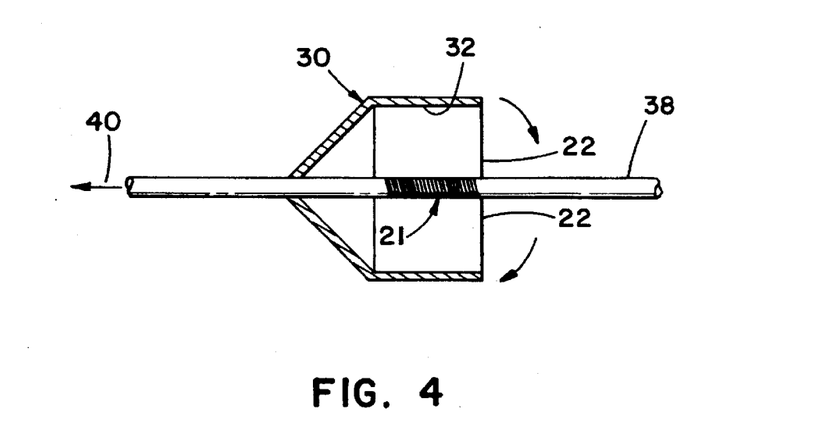
FIG. 4 is an elevational schematic illustration showing a multiple filament jig winding filaments onto a mandrel in accordance with the principles of the present invention.
Figure 5:
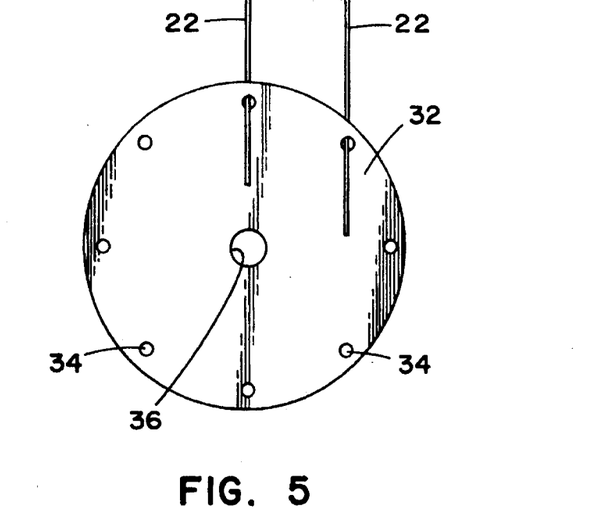
FIG. 5 is an elevational view of an embodiment of a multifilament jig which might be used in accordance with the principles of the present invention.

Illustrated in FIGS. 4 and 5 is one method for making the flexible tubular member 20 embodiment shown in FIGS. 1–3. As shown in FIG. 4, a jig 30 has a portion 32 with apertures 34 disposed therein generally about its periphery. The filaments 22 are slidably disposed in the apertures 34 and are fed from supply reels or the like (not shown). The center of the jig 30 has an aperture 36 for insertion therethrough of a mandrel 38. The mandrel 38 would typically have a diameter of one inch or less. The ends of the filaments 22 are suitably attached to the mandrel 38 at the beginning of the winding process. It will be appreciated that the jig 30 might take on any number of suitable configurations. For example, as opposed to apertures, guide arms might be used to guide the filaments. Moreover, the jig might be replaced with a plurality of arms which are movable radially toward and away from the mandrel.

As illustrated in FIG. 4, the mandrel 38 is inserted through the aperture 36 in the jig 30 and the mandrel 38 is rotated as the mandrel 38 is moved in a downstream direction as generally indicated by the arrow 40. As a result, the filaments 22 are wound onto the mandrel so as to form the single layer multiwire coil 21. The filaments 22 are maintained under very high tension as they are wound onto the mandrel. The tension of course will vary depending on a number of factors. Varying the rate of rotation and the rate of longitudinal movement will result in varying configurations of coils.

The coil 21 is then encased in a suitable low friction material as noted above so as to form a coated flexible tubular member 20 for use as a catheter, guidewire, catheter sheath or drug infusion catheter/guidewire. In one embodiment, the mandrel is moved longitudinally and is rotated, although the jig could just as well be moved and rotated. A typical speed of movement might be one inch per minute, while a typical rate of rotation might be ten revolutions per minute (RPM).

A programmable controller might be used to control the operation of the jig 30 and the mandrel 38 so as to enable precise control of the winding process such that very specific coil configurations can be achieved as well as variations thereof. Those skilled in the art would recognize that several other well known coil winding methods could be used with the invention.

Illustrated in FIGS. 6–10 are alternative embodiments of the flexible tubular member 20 for use as a catheter, guidewire, catheter sheath or drug infusion catheter/guidewire. These embodiments comprise a single metal tube 50, with a wall thickness of roughly 0.001 inches to 0.010 inches. The tube 50 has a plurality of slots 52 disposed therein to form a flexible tubular member 20. The preferred tube material would be stainless steel or nitinol, however, the tube material could be spring temper steel such as the product brand ELGILOY®, or another suitable alloy material. The tube 50 is encased in a suitable low friction material as noted above for the embodiments shown in FIGS. 1–3 so as to seal off the slots making it fluid tight. The inner surface of the tube 50 is preferably coated with a similar low friction material such as TEFLON®, PTFE or FEP so as to provide low friction. Typically the thickness of the outer and inner coating will be 0.001 inches to 0.003 inches or less. It will be appreciated that by varying the configuration of the slots, their depth, and the spacing between the slots, the flexibility, longitudinal stiffness and hoop strength of the flexible tubular member 20 can be varied. In addition, the variation of the composition and thickness of the coating material will also vary the flexibility of the coated flexible tubular member 20 for use as a catheter, guidewire, catheter sheath or drug infusion catheter/guidewire. Moreover, the metal tube 50 might be bent and heat treated to pre-form curves and configurations as desired.

In one embodiment, the slots are cut totally through the tubing wall 50 by use of a an electrostatic discharge machining tool (EDM). To cut the slots using the EDM machine, both ends of the tube 50 are fastened to a holding device such that the tube 50 is positioned between two or more EDM wires. The holding device would then position the tube 50 at the desired location for cutting a slot. The EDM wires would then be moved inward to cut the desired slot. The EDM wires would then translate outward beyond the outer diameter of the tube 50. The holding device would then rotate and/or translate the tube 50 to the desired position for cutting another set of slots. The EDM wires would then be moved inward to cut the next set of slots. This procedure would be repeated throughout the tube 50 to create a flexible tubular member 20. Those skilled in the art would recognize that multiple holding devices and multiple EDM wires could be used to simultaneously cut multiple slots into multiple tubes 50 to simultaneously create multiple flexible tubular members 20.

Figure 17:
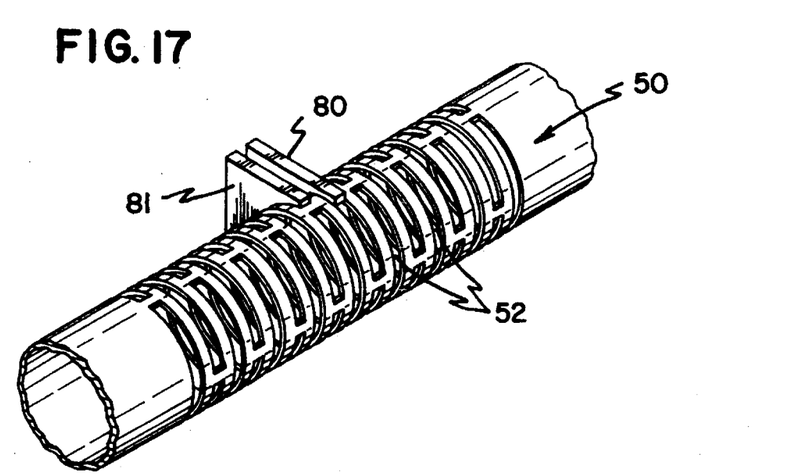
FIG. 17 is a partial perspective view of an alternate embodiment of a catheter, guidewire, catheter sheath or drug infusion catheter/guidewire made in accordance with the principals of the present invention wherein slots are cut into a wall of a thin-walled tube by electrodes from an electrostatic discharge machining tool.

In the preferred embodiment, the slots are cut totally through the tubing wall 50 by use of a plunge EDM machine. As recognized by those skilled in the art, a plunge EDM machine utilizes charged electrodes that are arranged and configured to cut a predetermined shape when they are plunged into a base material. As shown in FIG. 17, a plunge EDM machine with first and second electrodes 80, 81 can be utilized to cut an alternating pattern of slots 52 in the thin-walled tube 50 that are offset by 90°.

Figure 18:
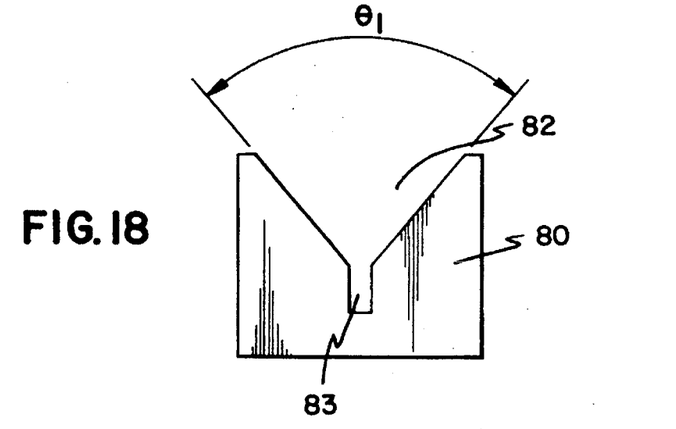
FIG. 18 is a side elevational view of a first electrode for cutting slots in a thin-walled tube as shown in FIG. 17.

As shown in FIG. 18, the first electrode 80 would be generally rectangular in shape with a notch 82 that is triangular in shape with a rectangular extension 83. The depth of the notch 82 would be greater than the radius of tube 50 such that a portion of the tube 50 would be displaced within the rectangular extension 83 of the notch 82 when the first electrode 80 is plunged into the tube 50. Because a portion of the tube 50 is displaced within the rectangular extension 83, that portion is not in contact with the first electrode 80 and is not cut. One example of a first electrode 80 for cutting slots 52 as shown in FIG. 17 would have an angle θ1 of 82° and a rectangular extension 83 with a width of 0.010 inches.

Figure 19:
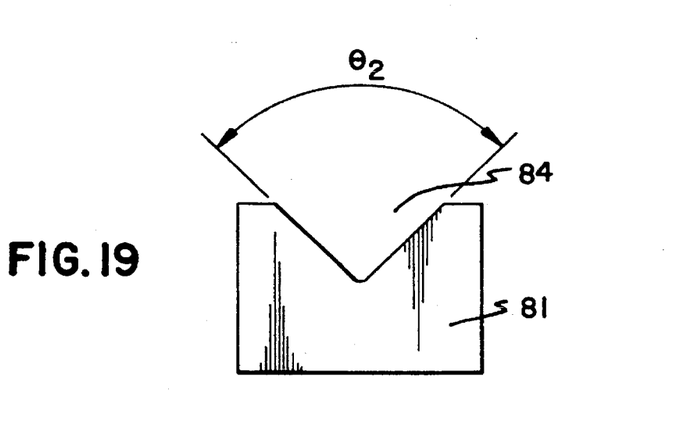
FIG. 19 is a side elevational view of a second electrode for cutting slots in a thin-walled tube as shown in FIG. 17.

As shown in FIG. 19, a second electrode 81 would be generally rectangular in shape with a triangular notch 84. The triangular notch 84 would have a depth that is less than the radius of the tube 50 and an angle θ2 that is more than 90°, preferably 94°. Because the depth of the triangular notch 84 is less than the radius of the tube 50, a portion of the tube 50 will extend beyond the second electrode 81 as shown in FIG. 17 and will not be cut.

In the preferred embodiment, a second pair of first and second electrodes (not shown) would be oppositely disposed from the first and second electrodes 80, 81 shown in FIG. 17. First, the tube 50 would be secured on both ends. Then, the first pair of electrodes would be plunged into the tube 50 to cut half of a pair of slots 52 as shown in FIG. 17. Then, the first pair of electrodes would be removed and the second pair of electrodes would be plunged into the tube 50 to complete the creation of the pair of slots 52 as shown in FIG. 17. Those skilled in the art would recognize that multiple pairs of electrodes 80, 81 could be displaced along the length of the tube 50 to cut a predetermined pattern of multiple slots 52 in the tube 50 without having to translate either the tube 50 or the electrodes 80, 81. Those skilled in the art would also recognize that other electrode configurations could be used to cut other patterns of slots in the tube 50. Moreover, those skilled in the art would recognize that a laser or other suitable slot cutting tools such as wet chemical and acid etching tools could be used with the present invention.

In some embodiments, the slots 52 or apertures need not be cut completely through the tubing wall 50. Such apertures could also be referred to as "slits" "notches" or "etches."It will be appreciated that the flexible tubular member 20 might be manufactured in any number of ways in keeping with the principles of the invention. For example, holes of a suitable pattern might be cut in a flat sheet of material such as stainless steel or nitinol which is then rolled and welded into the appropriate shape. In yet other methods, holes of a suitable pattern might be cut in a thicker, shorter tube of metal which is then drawn into an appropriate shape.

Figure 6:
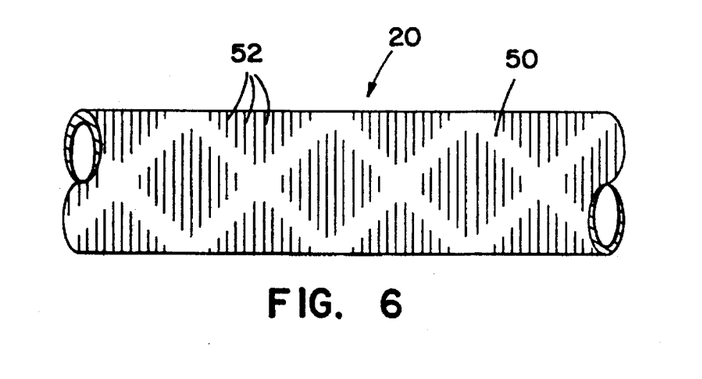
FIG. 6 is a partial side elevational view of an alternate embodiment of a catheter, guidewire, catheter sheath or drug infusion catheter/guidewire in accordance with the principles of the present invention wherein slots are cut into a wall of a thin walled tube.
Figure 7:
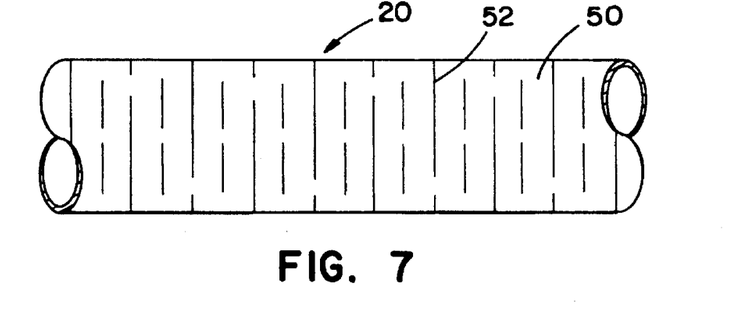
FIG. 7 is a view similar to FIG. 6 illustrating the slots being spaced further apart.
Figure 8:
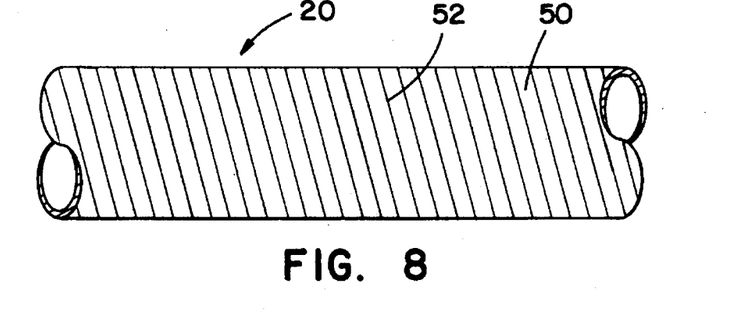
FIG. 8 is a view similar to FIG. 7 illustrating the slots being spaced closer together and continuous.

In FIGS. 6–8 the slots are shown as running generally transverse to the longitudinal axis of the flexible tubular member 20. The flexible tubular member 20 shown in FIG. 6 is more flexible than the flexible tubular member 20 shown as FIG. 7 as the slots 52 are closer together. One example of the spacing between slots is 0.05 to 0.10 inches. The flexible tubular member 20 of FIG. 8 has a continuous slot in a spiral and is very flexible.

Figure 9:
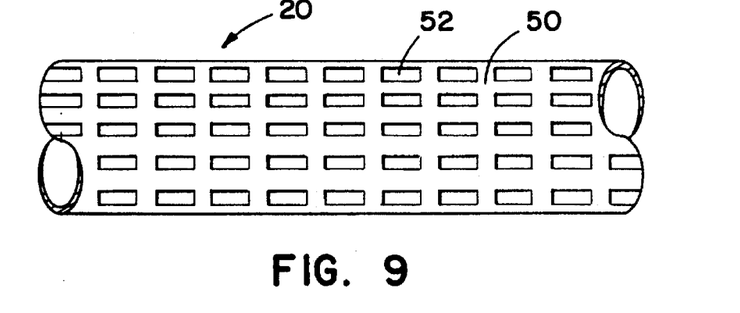
FIG. 9 is a partial side elevational view of a catheter, guidewire, catheter sheath or drug infusion catheter/guidewire in accordance with the principles of the present invention wherein longitudinally extending slots have been cut into the catheter, guidewire, catheter sheath or drug infusion catheter/guidewire.
Figure 10:
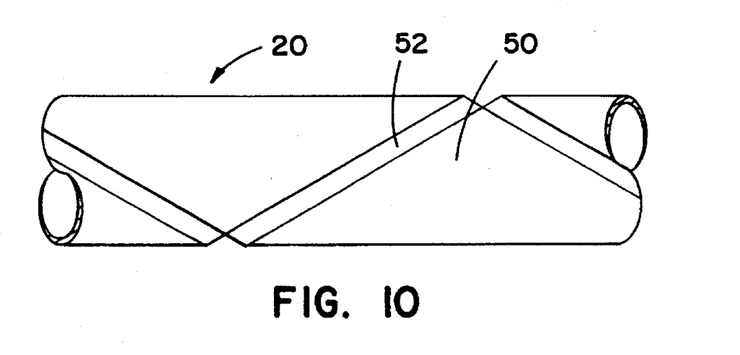
FIG. 10 is a view similar to FIG. 9 illustrating an alternate embodiment of a catheter, guidewire, catheter sheath or drug infusion catheter/guidewire wherein a helical slot has been cut in the wall of the catheter, guidewire, catheter sheath or drug infusion catheter/guidewire.

In FIG. 9, an alternate embodiment is shown wherein the slots 52 extend longitudinally of the tube 50. In FIG. 10, a slot 52 is shown as extending helically about the tube 50. It will be appreciated that any number of different slot configurations might be created in the tube 50. Moreover, the configuration of the slots might be varied along the length of the tube 50 so as to provide a flexible tubular member 20 with varying characteristics along its length.

A further explanation of the invention for use as a catheter, including a guide catheter or balloon catheter, a guidewire, a catheter sheath or drug infusion catheter/ guidewire is provided hereinafter.

Catheters

As described earlier, the various embodiments of the invention can be used as catheters. The inside and outside diameters of the catheters may vary, however, some catheters have an outside diameter from 0.010 inches to 0.250 inches or larger. The use of the invention as a catheter is particularly advantageous because one can make a catheter having varied characteristics along its length. For example, the distal end of the catheter typically must be very flexible, while other areas of the catheter must be stiffer to provide the longitudinal stiffness to transmit the torque required to maneuver the catheter. These requirements can be met by varying the windings of the coils 21 or by welding adjacent windings of the coil 21 as described in the first embodiment of the invention or by varying the configuration of the slots 52 in the flexible tubular member 20 as described in the second embodiment of the invention.

Figure 11:
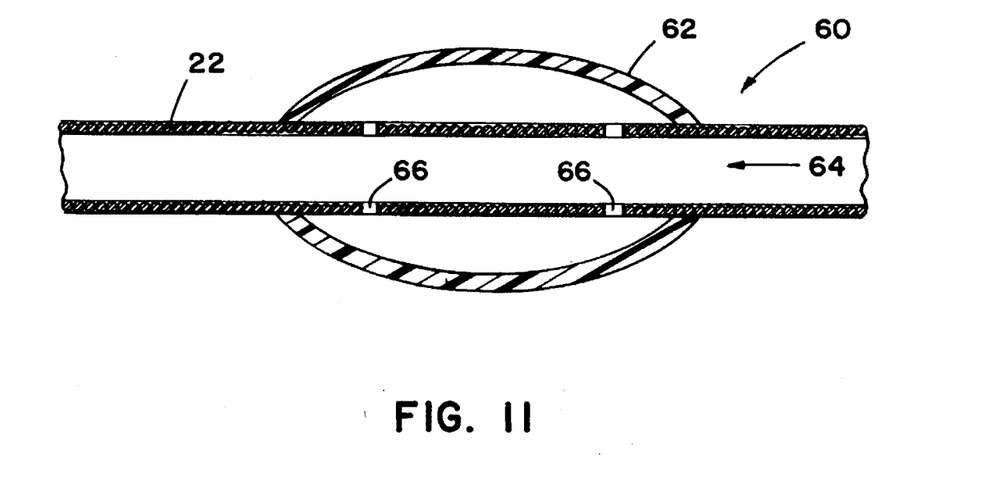
FIG. 11 is a sectional view of a balloon catheter comprising a catheter made from the embodiment shown in FIG. 1.

FIG. 11 illustrates a balloon type catheter 60 utilizing an embodiment of the flexible tubular member 20 for use as a catheter shown in FIG. 1. The balloon catheter 60 includes an expandable balloon portion 62 interconnected to lumen 64 of the catheter 20 by ports 66. The balloon portion is expanded to temporarily obstruct the passageway of a coronary artery or the like during angioplasty treatment.

Guidewires

As described earlier, a coated flexible tubular member 20 in accordance with the invention can be used as a guidewire. The guidewires that are currently used are comprised of a core wire that is welded to the inner surface of a spring coil. TEFLON® is then spray coated on the outside of the device to complete the assembly of the guidewire. However, in order to make these guidewires steerable, the core wire has a series of elaborate tapering schemes to vary the stiffness and flexibility of the various portions of the guidewire.

Figure 20:
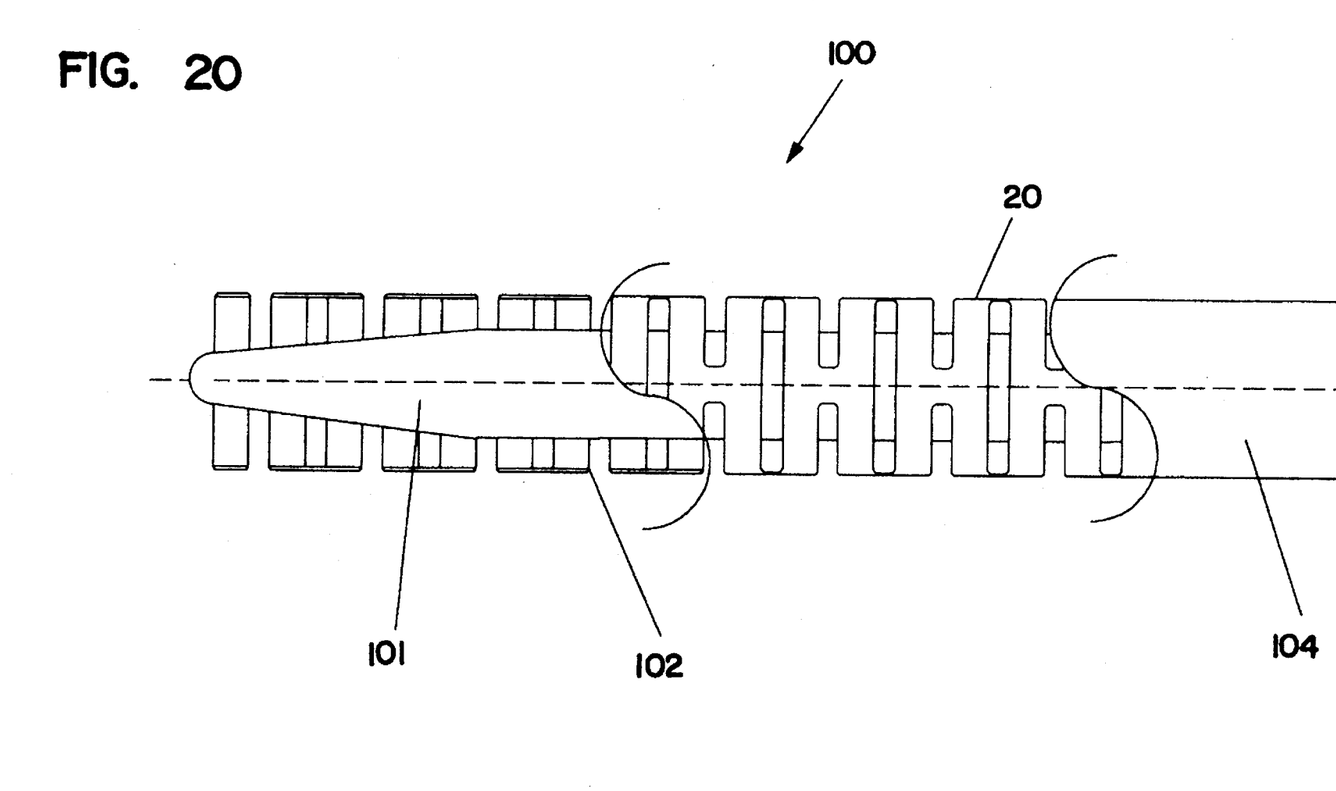
FIG. 20 is a partial cross sectional view of a representative guidewire according to the present invention.

As shown in FIG. 20, a guidewire 100 made according to the present invention would be comprised of a core wire 101 that is attached to a flexible tubular portion 20 made according to any of the previously described embodiments of the invention. In FIG. 20, the following configuration is shown by way of example: a core wire 101 attached to the distal end of the guidewire 100 a slotted tubular portion 102. However, various other guidewire configurations could be employed within the scope of the present invention. The outer surface of the tubular member 20 is covered with an appropriate biocompatible encasing 104 as described hereinabove. The length of these guidewires would typically range from 150 centimeters to 300 centimeters and the flexible tubular member 20 would have an outside diameter between 0.010 and 0.065 inches.

By varying the flexibility of the flexible tubular member 20 along the length of the guidewire as described above, a guidewire in accordance with the present invention can achieve the functions of current guidewires without the need for elaborate tapering schemes for the core wire. For example, as described in the first embodiment, the distal end of the guidewire could be made very flexible by using a coil 21 with more longitudinally displaced windings, while the proximal end of the guide wire could be made stiffer by having more circular windings or by welding adjacent windings together. As previously described in the second embodiment, the same result could be achieved by varying the configuration of the slots 52 in the tube 50.

Catheter Sheaths and Catheter Introducers

As described earlier, a coated flexible tubular member 20 in accordance with the invention could also be used as a catheter sheath. The inside and outside diameter of catheter sheaths may vary to meet different introducer and catheter requirements; however, several embodiments of a catheter sheath have an outside diameter from 0.050 inches to 0.300 inches or larger. As described earlier, catheter sheaths require a high hoop strength at the distal end to prevent burring and notching and flexibility in the center portion to prevent kinking. To meet the requirements, the windings of the coil 21 in the first embodiment of the invention can be varied or welded to provide a high hoop strength at the distal end of the catheter sheath and the center portion of the catheter sheath can be made flexible to prevent kinking. Likewise, the configuration of the slots 52 in the tube 50 of the second embodiment can be varied to produce the same characteristics.

Figure 12:
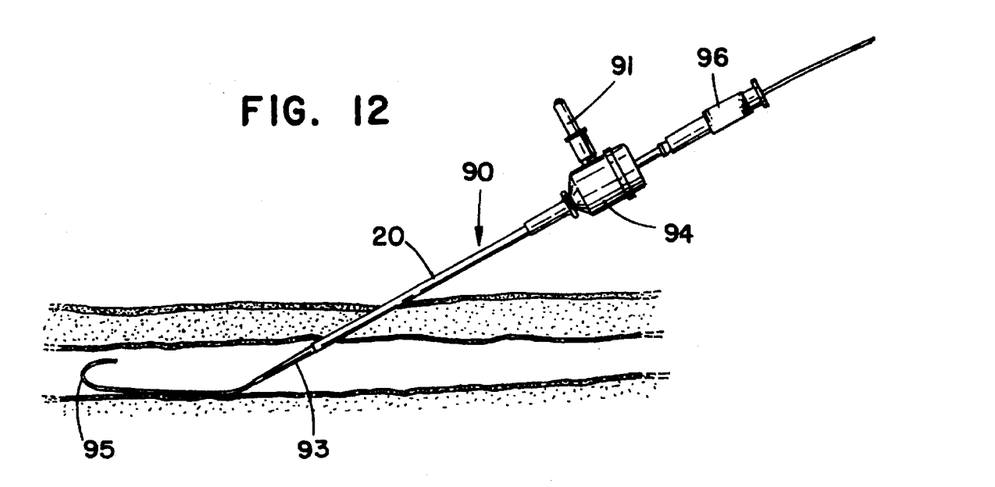
FIG. 12 is an elevational view with portions broken away of a catheter introducer, a guidewire and dilator after they have been advanced into the blood vessel of a patient.
Figure 13:
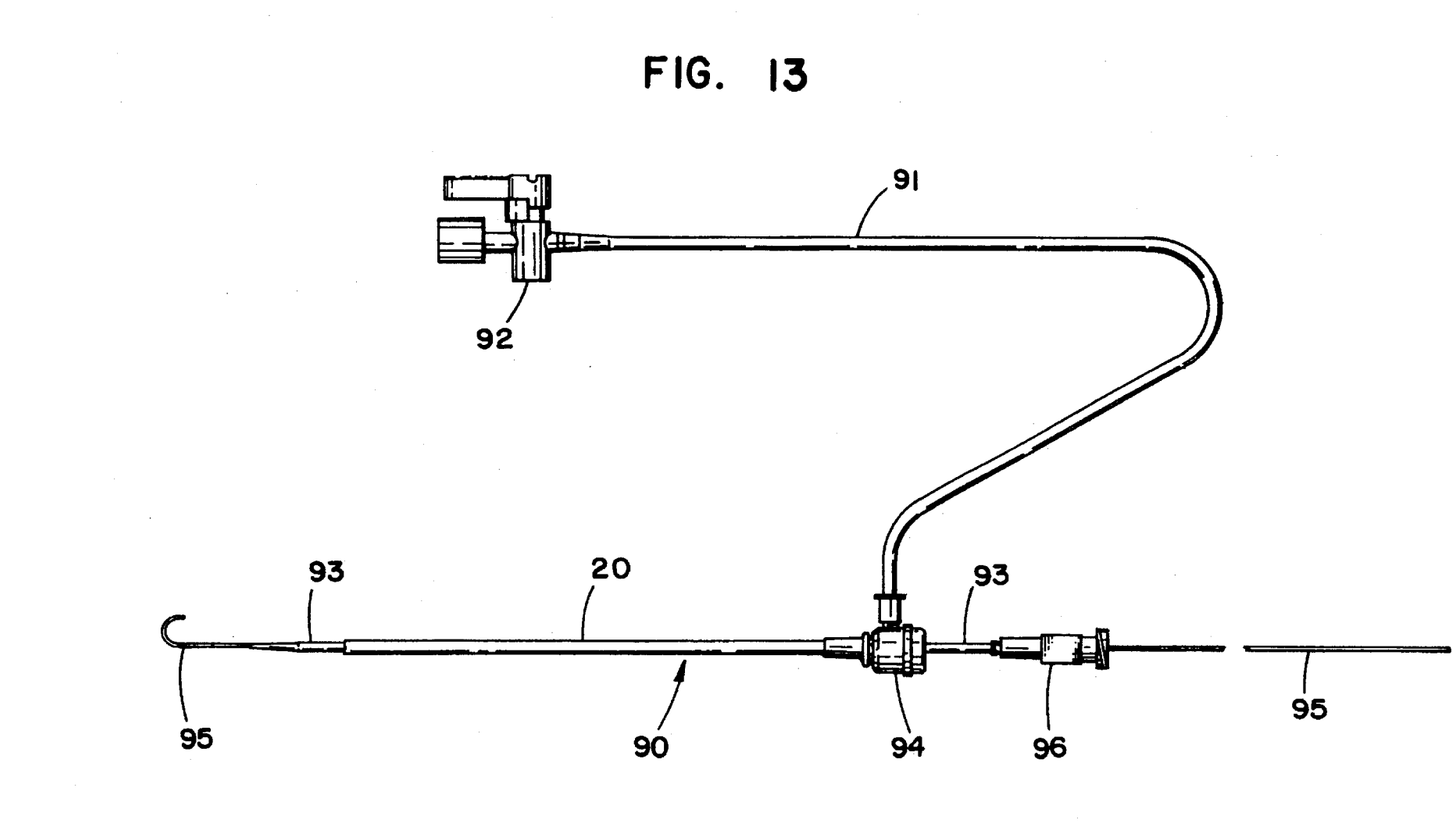
FIG. 13 is an elevational view of the catheter introducer having a fluid introduction tube and having a dilator and guidewire inserted therein.

As shown in FIGS. 12 and 13, a coated flexible tubular member 20 according to the present invention for use as a catheter sheath can be incorporated into a catheter introducer, generally designated as 90. In the preferred embodiment, the introducer 90 would have a hub 94 with hemostasis valve means that is connected to the coated flexible tubular member 20 (catheter sheath) and to a feed tube 91 having a three-way stop cock 92. Those skilled in the art will recognize that any hemostasis valve means such as those disclosed in U.S. Pat. Nos. 4,000,739 and 4,610,665 could be used with the present invention. The feed tube 91 is arranged and configured to allow the insertion of fluids through the hub 94 and catheter sheath 20 and into the patient's blood vessel.

The hub 94 and catheter sheath 20 are also arranged and configured to allow the insertion of a dilator 93 through the lumen of the hub 94 and catheter sheath 20. The dilator 93 would contain a lumen that is arranged and configured to allow the insertion of a guidewire 95 through the dilator 93. In the preferred embodiment, the dilator 93 is generally cylindrical in shape with a tapered distal end and having a stop portion 96 generally located at its proximal end that is arranged and configured to temporarily secure the dilator 93 to the hub 94. The dilator 93 also has an outer diameter that is approximately equal to the diameter of the lumen in the catheter sheath 20 so as to provide an interference fit to support the catheter sheath 20 during its insertion into the blood vessel. Those skilled in the art would recognize that other dilators 93 could be used with the invention.

Drug Infusion Catheter/Guidewires

Figure 15:
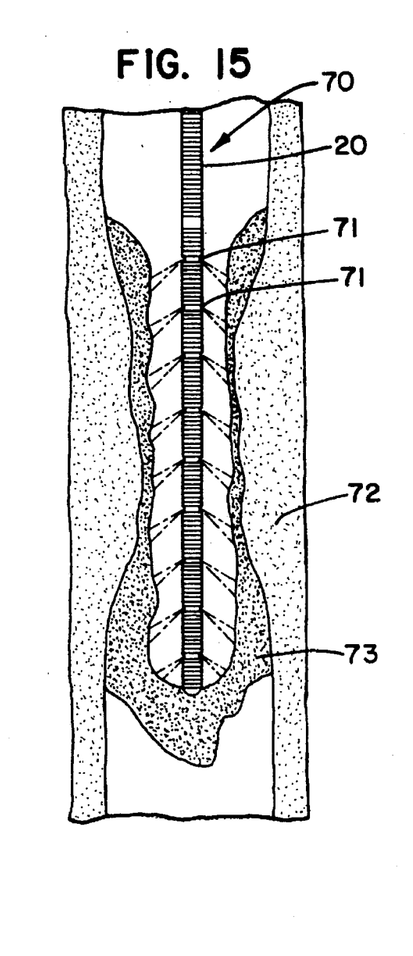
FIG. 15 is an elevational view of a representative guidewire type drug infusion catheter/guidewire with portions broken away after it has been advanced into a blood vessel of a patient and the core has been withdrawn.

As described earlier, drug infusion catheter/guidewires can also be made according to the present invention. As shown in FIG. 15, a guidewire type drug infusion catheter/guidewire 70 is located within the lumen of a blood vessel 72 with occlusion 73. The guidewire type drug infusion catheter/guidewire 70 would be comprised of a flexible tubular member 20 made in accordance with the previously described invention having side holes 71 near its distal end and a removable core wire (not shown). Like guidewires, the flexible tubular member 20 would have a small outside diameter ranging between 0.01 and 0.05 inches.

Figure 16:
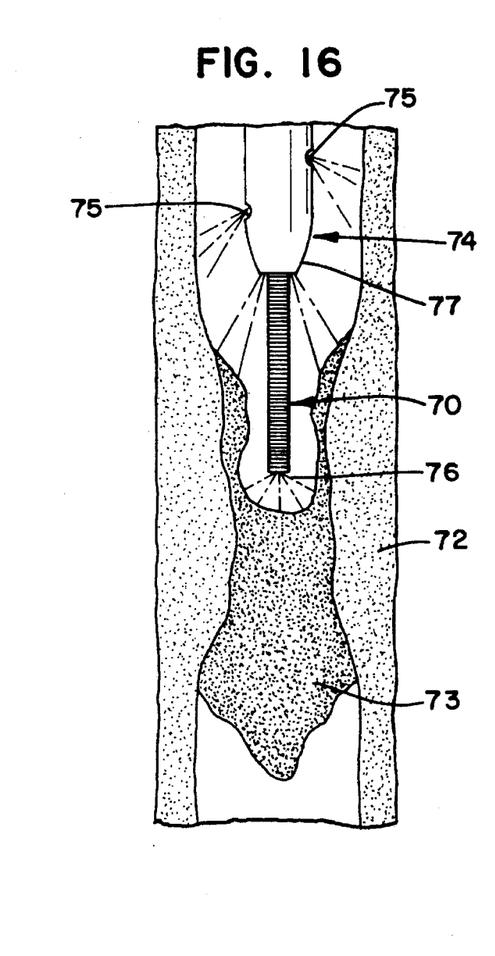
FIG. 16 is an elevational view of a representative combination catheter type and end hole guidewire type drug infusion catheter/guidewire device with portions broken away after it has been advanced into a blood vessel of a patient and the core wire has been withdrawn.

In use, the flexible tubular member and removable core would be advanced together through the patient's circulatory system like a conventional guidewire until reaching the desired location. Therefore, the use of a flexible tubular member 20 in accordance with the various embodiments of the invention previously described in the discussion on guidewires provides the guidewire type drug infusion catheter/guidewire with the required flexibility and torquability to maneuver the device through the circulatory system. After reaching the desired location, the core is removed leaving only the flexible tubular member 20 within the patient. Drugs or other fluids can then be pumped through the lumen of the flexible tubular member 20 and out the holes 71 and into the occluded portion of the blood vessel 72. As shown in FIG. 16, a second embodiment of a guidewire type drug infusion catheter/guidewire 70 could be made very similar to the previously described device in FIG. 15 except that the second embodiment would contain a hole in the distal end 76 and would not contain side holes 71 as shown in FIG. 15.

However, because the outside diameters of the flexible tubular member 20 in the guidewire type drug infusion catheter/guidewire devices are sized like guidewires, the lumen size of the flexible tubular member is limited. Therefore, the flowrate of drugs through the lumen is limited. If a larger flowrate or if a similar flowrate must be supplied with a lower source pressure, a catheter type drug infusion catheter/guidewire 74 might be used. The catheter type drug infusion catheter/guidewire 74 would be comprised of a flexible tubular member 20 made in accordance with the previously described embodiments of the invention for use as a catheter, except that it would have a tapered distal end 77 and side holes 75 near its distal end 77. The catheter type drug infusion catheter/guidewire 74 would be advanced over a guidewire or a guidewire type drug infusion catheter/guidewire 70, as shown in FIG. 16. Upon reaching the desired location, drugs or other fluids would be pumped through the catheter type drug infusion catheter/guidewire 74 and through the side holes 75 into the blood vessel near the occluded location. Because the catheter type drug infusion devices 74 have a larger lumen than the guidewire type drug infusion devices 70, the drugs or other fluids can be delivered to the desired area at a lower pressure.

It is to be understood, however, that even though numerous characteristics and advantages of the present invention have been set forth above in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. An apparatus for use as a biocompatible medical device for insertion into vessels of the body comprising:
    a) a self-supporting tube having a plurality of apertures formed therein to increase the flexibility of the tube; and
    b) an encasing covering the tube so as to provide a fluid-tight seal.

2. An apparatus for use as a biocompatible medical device according to claim 1, wherein the tube is made of metal and the encasing is made of a biocompatible low-friction material.

3. An apparatus for use as a biocompatible medical device according to claim 2, wherein the metal is stainless steel.

4. An apparatus for use as a biocompatible medical device according to claim 2, wherein the metal is nitinol.

5. An apparatus for use as a biocompatible medical device according to claim 1, wherein the tube includes an inner wall which is coated with a biocompatible low-friction material.

6. An apparatus for use as a biocompatible medical device according to claim 1, wherein the configuration of the apertures is varied longitudinally so as to vary the longitudinal and torsional flexibility characteristics along the tube.

7. An apparatus for use as a biocompatible medical device according to claim 1, wherein the depth of the apertures is varied longitudinally so as to vary the longitudinal and torsional flexibility characteristics along the tube.

8. An apparatus for use as a biocompatible medical device according to claim 1, wherein the apertures extend completely through the tube.

9. An apparatus for use as a biocompatible medical device according to claim 1, wherein the apertures include transverse slots.

10. An apparatus for use as a biocompatible medical device according to claim 1, wherein the apertures include longitudinal slots.

11. An apparatus for use as a biocompatible medical device according to claim 1, wherein the tube is continuous.

12. An apparatus for use as a biocompatible medical device according to claim 1, wherein the biocompatible medical device is a catheter.

13. An apparatus for use as a biocompatible medical device according to claim 1, wherein the biocompatible medical device is a catheter sheath.

14. An apparatus for use as a biocompatible medical device according to claim 1, wherein the biocompatible medical device is a catheter sheath introducer.

15. An apparatus for use as a biocompatible medical device according to claim 1, wherein the biocompatible medical device is a guidewire.

16. An apparatus for use as a biocompatible medical device according to claim 1, wherein the biocompatible medical device is a fixed core guidewire.

17. An apparatus for use as a biocompatible medical device according to claim 1, wherein the biocompatible medical device is a balloon catheter.

18. An apparatus for use as a biocompatible medical device for insertion into vessels of the body comprising:
   a) a self-supporting tube having a longitudinally extending spiraled aperture cut therein to increase the flexibility of the tube; and
   b) an encasing covering the tube so as to provide for a fluid-tight seal.

* * * * *